US009963712B2

(12) United States Patent
Bae et al.

(10) Patent No.: US 9,963,712 B2
(45) Date of Patent: May 8, 2018

(54) GENE IBENOD93 AND TRANSGENIC PLANTS USING THE SAME

(71) Applicant: Korea University Research and Business Foundation, Seoul (KR)

(72) Inventors: Jung Myung Bae, Seoul (KR); Seol Ah Noh, Gyeonggi-Do (KR); Jeong Sheop Shin, Seoul (KR)

(73) Assignee: Korea University Research and Business Foundation, Seoul (KR)

(*) Notice: Subject to any disclaimer, the term of this patent is extended or adjusted under 35 U.S.C. 154(b) by 62 days.

(21) Appl. No.: 14/814,986

(22) Filed: Jul. 31, 2015

(65) Prior Publication Data

US 2016/0032302 A1 Feb. 4, 2016

(30) Foreign Application Priority Data

Aug. 1, 2014 (KR) ........................ 10-2014-0098721

(51) Int. Cl.
*C12N 15/29* (2006.01)
*C12N 15/82* (2006.01)

(52) U.S. Cl.
CPC ..... *C12N 15/8227* (2013.01); *C12N 15/8261* (2013.01); *Y02A 40/146* (2018.01)

(58) Field of Classification Search
None
See application file for complete search history.

(56) References Cited

U.S. PATENT DOCUMENTS

| | | | | |
|---|---|---|---|---|
| 7,273,967 B2 | 9/2007 | Bae et al. | | |
| 2006/0048246 A1* | 3/2006 | Bae | .................... | C12N 15/8227 800/287 |

OTHER PUBLICATIONS

Bi et al. Plant, cell & environment 32 (2009): 1749-1760.*
Genbank Accession No. BU690467 entered Feb. 20, 2003.*
Ulmasov et al. The Plant Cell, vol. 7, 1611-1623, Oct. 1995.*
Bi et al. Plant, cell & environment 32.12 (2009): 1749-1760.*
You et al. FEBS Letters 536 (2003) 101-105.*
Of Genbank Accession No. BU690467 entered Feb. 20, 2003.*
Choi, D. et al., Analysis of transcripts in methyl jasmonate-treated ginseng hairy roots to identify genes involved in the biosynthesis of ginsenosides and other secondary metabolites, Plant Cell Rep, 23; 557-66, 2005.
Clotault, J. et al., Expression of carotenoid biosynthesis genes during carrot root development, Journal of Experimental Botany, 59(13): 3563-73, 2008.
Han, J. et al., The Cyt P450 Enzyme CYP716A47 Catalyzes the Formation of Protopanaxadiol from Dammarenediol-II During Ginsenoside Biosynthesis in Panax ginseng, Plant Cell Physiol. 52(12): 2062-73, 2011.
Han, J. et al., Cytochrome P450 CYP716A53v2 Catalyzes the Formation of Protopanaxatriol from Protopanaxadiol During Ginsenoside Biosynthesis in Panax ginseng, Plant Cell Physiol. 53(9): 1535-45, 2012.
Jung, J. et al., Discovery of genes for ginsenoside biosynthesis by analysis of ginseng expressed sequence tags, Plant Cell Rep, 22: 224-30, 2003.
Just, B. et al., Carotenoid biosynthesis structural genes in carrot (*Daucus carota*): isolation, sequence-characterization, single nucleotide polymorphism (SNP) markers and genome mapping, Theor Appl Genet, 114: 693-704, 2007.
Ku, A. et al., IbMADS1 (*Ipomoea batatas* MADS-box 1 gene) is Involved in Tuberous Root Initiation in Sweet Potato (*Ipomoea batatas*), Annals of Botany, 102: 57-67, 2008.
Li, C. et al., Transcriptome analysis reveals ginsenosides biosynthetic genes, microRNAs and simple sequence repeats in Panax ginseng C.A. Meyer, BMC Genomics, 14: 245, 2013.
Noh, S. et al., SRD1 is involved in the auxin-mediated initial thickening growth of storage root by enhancing proliferation of metaxylem and cambium cells in sweet potato (*Ipomoea batatas*), Journal of Experimental Botany, 61(5): 1337-49, 2010.
Noh, S. et al., A sweetpotato SRD1 promoter confers strong root-, taproot-, and tuber-specific expression in *Arabidopsis,* carrot, and potato, Transgenic Res, 21: 265-78, 2012.
Noh, s. et al., Down-regulation of the IbEXP1 gene enhanced storage root development in sweetpotato, Journal of Experimental Botany, 64(1): 129-42, 2013.
Sun, C. et al., De novo sequencing and analysis of the American ginseng root transcriptome using a GS FLX Titanium platform to discover putative genes involved in ginsenoside biosynthesis, BMC Genomics, 11: 262, 2010.
Tanaka, M. et al., Analysis of genes developmentally regulated during storage root formation of sweet potato, Journal of Plant Physiology, 162: 91-102, 2005.

(Continued)

*Primary Examiner* — Shubo (Joe) Zhou
*Assistant Examiner* — Charles Logsdon
(74) *Attorney, Agent, or Firm* — Dinsmore & Shohl LLP

(57) ABSTRACT

The present invention relates to a novel gene, IbENOD93, and transgenic plants using the same. More specifically, the present invention provides an IbENOD93 gene, an open reading frame (ORF) of the IbENOD93 gene, a recombinant vector comprising the gene or the ORF, and a transformant transformed with the vector. Moreover, the present invention provides a composition for enhancing root thickening growth and promoting maturation in a plant having storage root(s). Furthermore, the present invention provides a method for producing a transgenic plant having storage root(s) with enhanced thickening growth, and a method for regulating or enhancing root thickening growth and maturation in a plant having storage root(s). According to the present invention, it is possible to promote the thickening growth of storage roots as well as the growth of aerial part. Therefore, the present invention can be effectively used to promote the thickening growth of storage roots of high-value root crops such as ginseng, sweet potato, etc. and to produce early-maturing transgenic plants.

2 Claims, 7 Drawing Sheets

(56) References Cited

OTHER PUBLICATIONS

Tanaka, M. et al., Expression of class 1 knotted1-like homeobox genes in the storage roots of sweetpotato (*Ipomoea batatas*), Journal of Plant Physiology, 165: 1726-35, 2008.

Tansakul, P. et al., Dammarenediol-II synthase, the first dedicated enzyme for ginsenoside biosynthesis, in Panax ginseng, FEBS Letters, 580: 5143-49, 2006.

You, M. et al., Identification of genes possibly related to storage root induction in sweetpotato, FEBS Letters, 536: 101-5, 2003.

* cited by examiner

FIG. 1A
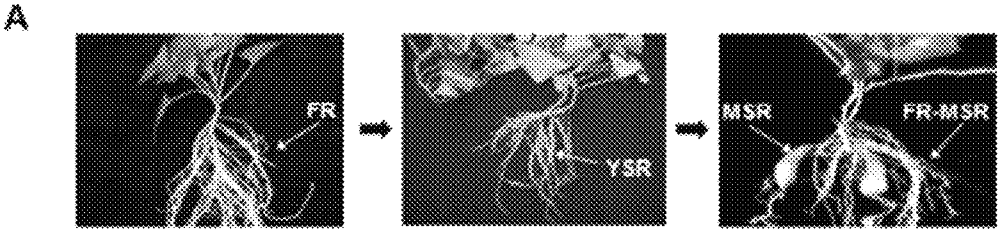
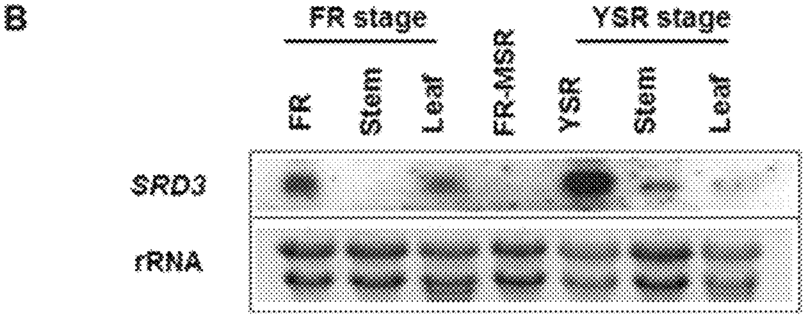
FIG. 1B

Control IbENOD93

SEQUENCE LISTING

```
<160> NUMBER OF SEQ ID NOS: 16

<210> SEQ ID NO 1
<211> LENGTH: 577
<212> TYPE: DNA
<213> ORGANISM: Ipomoea batatas

<400> SEQUENCE: 1

ggcacgagga ttgaacaaaa catagctttt tcttgaattt gactacttca gctcttcgtt     60

tgtatcagca atataatggc gggcaagaat gtgagtttgg cttctttgga ccagaggttg    120

gccatggcca aacgttgctc tcatgagggt gtagttgcag gcgctaaagc agctgtggct    180

gccaccattg caacagctat tccaacattg gctagtgtga gaatgctgcc atgggcaaga    240

gccaatttaa acccaacagc acaggcactg atagtctcaa cagccgctgg gatggcttac    300

ttcattgtgg ctgacaagac tgttcttgct acggctcgcc gcaactcctt caagaatggc    360

tcagtctccg ccaacattga tgcctgatct tgattatata ttattatatg catcatattt    420

tatctgatct ccctgctact caatcccatt catttcaaga aggggggtag ggggtggagt    480

tctgtttgga tgtatgacta ctgagtatga tgaatgatga atactgttgt atgaccaaca    540

atgtcctgtg aatataaaca aaaagttggt ttttccc                             577
```

<210> SEQ ID NO 2
<211> LENGTH: 103
<212> TYPE: PRT
<213> ORGANISM: Ipomoea batatas

<400> SEQUENCE: 2

```
Met Ala Gly Lys Asn Val Ser Leu Ala Ser Leu Asp Gln Arg Leu Ala
  1               5                  10                  15

Met Ala Lys Arg Cys Ser His Glu Gly Val Val Ala Gly Ala Lys Ala
             20                  25                  30

Ala Val Ala Ala Thr Ile Ala Thr Ala Ile Pro Thr Leu Ala Ser Val
         35                  40                  45

Arg Met Leu Pro Trp Ala Arg Ala Asn Leu Asn Pro Thr Ala Gln Ala
     50                  55                  60

Leu Ile Val Ser Thr Ala Ala Gly Met Ala Tyr Phe Ile Val Ala Asp
 65                  70                  75                  80

Lys Thr Val Leu Ala Thr Ala Arg Arg Asn Ser Phe Lys Asn Gly Ser
                 85                  90                  95

Val Ser Ala Asn Ile Asp Ala
            100
```

<210> SEQ ID NO 3
<211> LENGTH: 312
<212> TYPE: DNA
<213> ORGANISM: Ipomoea batatas

<400> SEQUENCE: 3

```
atggcgggca agaatgtgag tttggcttct ttggaccaga ggttggccat ggccaaacgt     60

tgctctcatg agggtgtagt tgcaggcgct aaagcagctg tggctgccac cattgcaaca    120

gctattccaa cattggctag tgtgagaatg ctgccatggg caagagccaa tttaaaccca    180

acagcacagg cactgatagt ctcaacagcc gctgggatgg cttacttcat tgtggctgac    240

aagactgttc ttgctacggc tcgccgcaac tccttcaaga atggctcagt ctccgccaac    300

attgatgcct ga                                                        312
```

<210> SEQ ID NO 4
<211> LENGTH: 3010
<212> TYPE: DNA
<213> ORGANISM: Artificial Sequence
<220> FEATURE:
<223> OTHER INFORMATION: SRD1 promoter

<400> SEQUENCE: 4

```
ggctggtttc taagacattt tttggtttaa tccaaaccta attacaaata ttcccaacaa     60

gatcgaatga tctatggcta caaaccctat cccaacaaaa aactacattt agtacatcaa    120

attaagtggc atgattattt tattttgttc gacaaagtag catcaaataa actacaaaaa    180

aaactacatc attacaaaaa gactaattat caggcatcaa tgttagtata tgggaggtgg    240

tgggttcgag cctcagtgga ggcgttgctg tctctttgtt cttcagtagg ttgagagagt    300

aatttatgaa cagatactac actgtaatag agtcagtagc aatcaaaaaa aaatttgttt    360

taataatatc ctaatattat atttttctaa ccagtactat gctttcggct ttccagaagg    420

cagaagccta aaaaattcaa ttaagtttat aaactttaat ccacttgttt gagtaattga    480

gtatctttca gaacggttgt agatttaggt gggatgacaa atggtattcc aaagttcaag    540

atatttcttt ttagatttag gaatttgtag tcttttaagg ttagaggtta cttaaaagga    600

tgaacaaatt ttttatccca ttctatttct aggaagaatt tataatccgt acgtgtgacg    660
```

-continued

```
gctgccatta attatagtgc ccattcattt ttattgggaa aaagtactca tccattattt    720
cattggcacg gcaacccagt tttaaatatt ttataacaat aataacatat ggaaccaaat    780
tgtaaccttt atatcccaca gacccacaca ttacacatcc aataaaactt gagccaaatt    840
atatattagc gttactgagt actgactaaa atatattttt aaaatatact aaaatattat    900
taaaaaaata ttaaaatagt aaaattatat taaatagaaa atttaattta atcaaagaat    960
accaactaaa acgtataaaa tgagaaaata taggtatata atattgatga ttccttttga   1020
ttttttttt atgatccgaa aattctttgg ccataagaag agtaaatgaa caatttaaac   1080
taagaaaata agtaagttgc tcctatgtga ttaatatata aagtgagatt tgagctgttg   1140
atctatatta ttgaattaga tcaacgactc aaaatgaagg ataatttttt taaaaaatcg   1200
cttcctgtta atattaatgc tttaaaatta agcacattaa actttaaaat aatgcacctt   1260
tttttttaat actattgacc ttgttacatg tagtatctga agtccaacaa agtcaacatt   1320
gtccccactg aggctcaaac ccgtgacctc ccactaggga gaatcgcttc atgccgcttg   1380
accacaagtc ctttggtaaa aataatgcac cttaaagatg taaacttacg catcttcgat   1440
gaactgacca ctttgagctt gcaacttata ctttttgaa gataagcttg taacttatta   1500
taatggtcta ttaacattaa aaaaaaaaaa agtttcacaa tcaaattata atatttgtag   1560
ccaaatgaat ttaccgcggg tgtgactatt caggaattta aatacactaa agttggaggg   1620
gtagtacact caatacacta ttgctcatga cttttttctt cttttttttt tagattagct   1680
aatatattaa tcccaaatag aaacgtttac accaaagttc gaaaaaatgt tgtgtcattt   1740
cttacagtta gacacaaaaa taacattttt agctaagtta cagtaaactt gattggcaga   1800
ctgtttcaca aattgggagc ttggatcctt gaaggaactt actgctttct tagagtcatt   1860
aatggtttgg ccaaacatag aaaagattag ttgagcagtc ttgcacacta cttgagtaat   1920
catctccatt cttctactta ttgacaatat tctcttatga aaaaacacac ttgatcttat   1980
atcagttagg gatttgaccg gtttattaaa ggatagccta ccaactttgt tgaacgacat   2040
atcatcatat catgattcaa aagatgctct tttttattgt catatttgtg gcacaggatg   2100
agtacagttt cgcatacacc atgatcattt ttatcaaatc atactctata aaaccctgtc   2160
aaagaaaaga gaggaagaaa cgagaagaag aaactcatcc aagaaacaag aggaacatta   2220
ttgctcatga ttagatcgac ttgaacatgt actaatgcca atctcaaatt acctacatag   2280
gtgtgttaga caaatatttg ttaattagct gattgactta atggatttga ctagttgtta   2340
acattaattg attgtaggaa attgtttggt aaattagttg ttagttgata gttgattaca   2400
tgaaaattac tttctcaaaa agcttatcga aaaaactatt ttgaacagct ttttgaattt   2460
taacatttta taacaataag ttgttacaaa aagctaatta atcaaatact catatccatt   2520
gtttaaccat gtcaaacaac taataataat taaataattt gtttttaaaa tataagttaa   2580
atttaattga taagctaact atattaccaa acataccgta atattttctt aaccgcggta   2640
tgggctaaga tatgattgta tactattttt gttgcgagca tgattaatac agtaatacca   2700
tcatttaaaa gtggaaacca cattcgcagc tgtttccgaa agcaaacagc taacatttgc   2760
taggttctta cttatgcatt aatctgggtt ataaaatccc catttccatg ttggtgtgaa   2820
caaccaccta aacctagcgt cttcaacaat tctaccctac tatcatcccc caagacttcc   2880
ccgaccagta aataacccgc tttcctcttt cagtgatttc ttcatttgac tttgctatat   2940
atatatataa tctgatctgc tttcatcttt cagtgatttc ttcatttgga tttcttcagg   3000
```

gaggagaagg 3010

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
aattaaccct cactaaaggg 20

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
cgggatatca ctcagcataa tg 22

<210> SEQ ID NO 7
<211> LENGTH: 40
<212> TYPE: DNA
<213> ORGANISM: Artificial Sequence
<220> FEATURE:
<223> OTHER INFORMATION: primer

<400> SEQUENCE: 7
gtctctagaa ttgaacaaaa catagctttt tcttgaattt 40

<210> SEQ ID NO 8
<211> LENGTH: 26
<212> TYPE: DNA
<213> ORGANISM: Artificial Sequence
<220> FEATURE:
<223> OTHER INFORMATION: primer

<400> SEQUENCE: 8
gtaggatccc atcaatgttg gcggag 26

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
catcatactc attactcata catccaaaca 30

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
cagtctccgc caacattgat g 21

<210> SEQ ID NO 11
<211> LENGTH: 21
<212> TYPE: DNA
<213> ORGANISM: Artificial Sequence -continued

```
<220> FEATURE:
<223> OTHER INFORMATION: primer

<400> SEQUENCE: 11

caactaccag ccaccaactg t                                          21


<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12

cagatcctca cgagcttcac                                            20


<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13

catcccggga ttgaacaaaa catagct                                    27


<210> SEQ ID NO 14
<211> LENGTH: 28
<212> TYPE: DNA
<213> ORGANISM: Artificial Sequence
<220> FEATURE:
<223> OTHER INFORMATION: primer

<400> SEQUENCE: 14

catgagctcc attgttggtc atacaaca                                   28


<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15

ggaacctctc aggctgattg tg                                         22


<210> SEQ ID NO 16
<211> LENGTH: 27
<212> TYPE: DNA
<213> ORGANISM: Artificial Sequence
<220> FEATURE:
<223> OTHER INFORMATION: primer

<400> SEQUENCE: 16

acaatttcct caaatctaga cttggaa                                    27
```

GENE IBENOD93 AND TRANSGENIC PLANTS USING THE SAME

CROSS-REFERENCE TO RELATED PATENT APPLICATION

This application claims the benefit of Korean Patent Application No. 10-2014-0098721, filed on Aug. 1, 2014, in the Korean Intellectual Property Office, the disclosure of which is incorporated herein in its entirety by reference.

BACKGROUND OF THE INVENTION

1. Field of the Invention

The present invention relates to a novel gene, IbENOD93, and transgenic plants using the same.

2. Description of the Related Art

In most dicotyledonous plants, the primary root develops from the seed at the beginning of growth, and the taproot develops from the primary root. In some plants such as ginseng, carrot, radish, etc., taproot-type storage roots are formed by secondary thickening growth due to continuous cell division and differentiation after the development of the primary root. The taproot-type storage roots store a large amount of carbohydrate that is an energy source for humans and animals, serve as a source of food fiber that is essential for human well-being life and, at the same time, produce secondary metabolites as raw materials for health supplements, which are thus considered economically important.

Meanwhile, in most high-value storage root crops such as ginseng, etc. the storage roots grow underground over several years. During the growth period, the storage roots are exposed to various pathogenic fungi, and thus their cultivation is likely to be stopped due to root rot disease before harvest time. Particularly, it is known that the cultivation of about 50% of storage roots is stopped due to root rot disease in cultivated fields of six-year old ginseng that is a typical high-value root crop in Korea. To minimize the damage to the cultivation of storage root crops, there is a need to develop the breeding of cultivars resistant to root rot disease as well as a molecular breeding method that can shorten the cultivation period of storage roots. Mining of genetic resources involved in the development of storage roots and a study on functional characterization of the genetic resources are prerequisites for the molecular breeding.

Recently, most of the molecular studies on the taproot-type storage roots have been focused on the isolation and characterization of genes involved in the synthesis of high-value secondary metabolites produced in taproot-type storage roots such as ginseng or carrot (Jung et al., 2003. Plant Cell Reports 22:224-230; Choi et al., 2005. Plant Cell Reports 23:557-566; Tansakul et al., 2006. FEBS Letter 580:5143-5149; Just et al., 2007. Theoretical and Applied Genetics 114:693-704; Clotault et al., 2008. Journal of Experimental Botany 59, 3563-3573; Sun et al., 2010. BMC Genomics 11:262; Han et al., 2011. Plant and Cell Physiology. 52:2062-2073, 2012 Plant Cell Physiol. 53:1535-1545; Li et al., 2013. BMC Genomics 14:245). However, the molecular mechanism involved in the development of taproot-type storage roots has not been reported, and the related genes have also not been found. Therefore, the molecular breeding to regulate the development of taproot-type storage roots has not been achieved.

The storage roots are divided into taproot-type storage roots such as carrot, ginseng, radish, etc. and tuberous storage roots such as sweet potato, which are different from each other in their shapes and development processes. The thickening growth of taproot-type storage roots such as carrot is caused by the continuous division in the vascular cambium of the primary roots, during which the secondary vascular tissue is formed, and the cortex and epidermis outside the secondary vascular tissue are peeled off. Therefore, most of the mature taproot-type storage roots consist of the secondary vascular tissue. Meanwhile, unlike the development process of taproot-type storage roots, the thickening growth of tuberous storage roots such as sweet potato is achieved by the development of several abnormal secondary vascular tissues in the primary vascular tissue. However, these storage roots of two types, which are different from each other in their shapes and development processes, are the same in that active cell division occurs in the vascular cambium during the thickening growth.

With the recent development of various molecular approaches, genes have been found that are believed to be involved in the development of storage roots of sweet potato, and as a result, genes have been identified that exhibit differential expression patterns in developing storage roots of sweet potato. (You et al., 2003, FEBS Letters 536, 101-105; Tanaka et al., 2005, Journal of Plant Physiology 162, 91-102; Tanaka et al., 2008, Journal of Plant Physiology 165, 1726-1735). However, the functional characterization of these genes involved in the development of storage roots has not been performed. Recently, the present inventors have found that the SRD1 gene, a MADS-box gene of sweet potato, promotes the cell division in the cambium and metaxylem of storage roots and thus is involved in promoting the thickening growth of storage roots (Noh et al., 2010, Journal of Experimental Botany 61: 1337-1349) and that the IbEXP1 gene inhibits the cell division in the cambium and metaxylem of storage roots and thus is involved in suppressing the thickening growth of storage roots (Noh et al., 2013, Journal of Experimental Botany 64:129-142). It is expected that these sweet potato genes will be used as genetic resources that can regulate the development of taproot-type storage roots such as carrot, etc.

Therefore, there has been a continuous demand for the production of early-maturing transgenic root crops using genes involved in the development of storage roots to increase the productivity of storage roots.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

SUMMARY OF THE INVENTION

An object of the present invention is to provide an IbENOD93 gene comprising the nucleotide sequence of SEQ ID NO.: 1.

Another object of the present invention is to provide an open reading frame (ORF) of an IbENOD93 gene comprising the nucleotide sequence of SEQ ID NO.: 3.

Still another object of the present invention is to provide an IbENOD93 protein encoded by a gene comprising the nucleotide sequence of SEQ ID NO.: 1 or an ORF comprising the nucleotide sequence of SEQ ID NO.: 3.

Yet another object of the present invention is to provide a recombinant vector comprising the gene or the ORF.

Still yet another object of the present invention is to provide a transformant transformed with the vector.

A further object of the present invention is to provide a composition for enhancing root thickening growth and promoting maturation in a plant having storage root(s).

Another further object of the present invention is to provide a method for producing a transgenic plant having storage root(s) with enhanced thickening growth.

Still further object of the present invention is to provide a method for regulating or enhancing root thickening growth and maturation in a plant having storage root(s).

The present inventors have made extensive efforts to find a gene that can enhance root thickening growth and promote maturation in a plant having storage root(s) and, as a result, found that a transgenic plant transformed with an IbENOD93 gene from sweet potato has storage root(s) with enhanced thickening and significantly promoted growth, thereby completing the present invention.

Next, the present invention will be described in detail.

According to an aspect of the present invention, the present invention provides an IbENOD93 gene comprising the nucleotide sequence of SEQ ID NO.: 1, which enhances root thickening growth and promotes maturation in a plant having a storage root.

The IbENOD93 gene of the present invention is a novel gene that has not yet been identified and is first identified by the present inventors (see Example 1).

According to a preferred embodiment of the present invention, the gene is derived from sweet potato (*Ipomoea batatas*) and provides a nucleic acid molecule comprising a nucleotide sequence encoding the corresponding protein.

Preferably, the nucleic acid molecule of the present invention is cDNA and comprises the nucleotide sequence of SEQ ID NO.: 1.

The nucleic acid molecule of the present invention may comprise a nucleotide sequence having substantial identity to the nucleotide sequence. The term "substantial identity" refers to a nucleotide sequence having at least 80% identity, more preferably at least 90% identity, most preferably at least 95% identity when aligning the above-described nucleotide sequence of the present invention with any other sequence to closely match each other and analyzing the aligned sequence using a commonly used program (e.g., DNASIS or ClustalX).

According to another aspect of the present invention, the present invention provides an open reading frame (ORF) of an IbENOD93 gene comprising the nucleotide sequence of SEQ ID NO.: 3.

As used herein, the term "open reading frame (ORF)" refers to a coding sequence (CDS) that serves as a template for protein synthesis.

According to still another aspect of the present invention, the present invention provides an IbENOD93 protein encoded by a gene comprising the nucleotide sequence of SEQ ID NO.: 1 or an ORF comprising the nucleotide sequence of SEQ ID NO.: 3.

According to a preferred embodiment of the present invention, the protein comprises the amino acid sequence of SEQ ID NO.: 2.

More specifically, according to the present invention, an expressed sequence tag (EST) library was constructed with total RNA isolated from young storage roots of sweet potato. A cDNA clone with high homology to an ENOD93 protein was isolated by screening the library and named IbENOD93.

Moreover, the nucleotide sequence of the cDNA consists of 577 bp, including a 5'-untranslated region of 75 bp, an open reading frame (ORF) of 312 bp (103 amino acids), and a 3'-untranslated region of 190 bp. The ORF nucleotide sequence was registered as "cDNA sequence of IbENOD93 cloned from sweetpotato" in the NCBI (NCBI accession no. KC915011).

According to yet another aspect of the present invention, the present invention provides a recombinant vector comprising the gene or the ORF.

The vector system of the present invention may be constructed using various methods known in the art, and suitable methods are disclosed in Sambrook et al., Molecular Cloning, A Laboratory Manual, Cold Spring Harbor Laboratory Press (2001) which is incorporated herein by reference.

The vector of the present invention may generally be constructed as a cloning vector or an expression vector. Moreover, the vector of the present invention may be constructed using a prokaryotic cell or a eukaryotic cell as a host.

In the present invention, the vector is a binary vector for transformation that can permanently express a foreign gene in a plant and is a recombinant expression vector specific for storage roots of a plant prepared by operatively linking a gene encoding a target protein downstream of a promoter.

The expression vector according to the present invention may be prepared by inserting a promoter of the present invention into a basic skeleton of a typical protein expression vector and inserting a nucleotide sequence encoding a target protein downstream of the promoter.

In an Example of the present invention, a pBI101 vector was used for the preparation of the expression vector.

Moreover, according to a preferred embodiment of the present invention, the recombinant vector comprises an SRD1 promoter comprising the nucleotide sequence of SEQ ID NO.: 4.

The promoter according to the present invention is an SRD1 promoter which specifically induces the expression of a gene in the storage root. Therefore, the promoter according to the present invention can induce the expression of a target gene in the storage root.

The promoter according to the present invention may have the nucleotide sequence of SEQ ID NO.: 4 as well as a nucleotide sequence with a substitution, deletion or addition of one or more bases in the nucleotide sequence of SEQ ID NO.: 4 and may exhibit promoter activity.

According to the present invention, in the sweet potato IbENOD93 cDNA, after removal of a GUS gene of the pBI101 vector, the IbENOD93 gene linked to the SRD1 promoter at the same position may be located in front of a NOS terminator. While the pBI101 vector was used in the present invention, it is apparent to those skilled in the art that it can be replaced with other plant transformation vectors.

The binary vector can transform a plant by a method using *agrobacterium* or a method using particle bombardment. For example, carrot is transformed using *agrobacterium* in the present invention.

According to still yet another aspect of the present invention, the present invention provides a transformant transformed with the vector.

The preparation of the transformant according to the present invention may be performed according to a method well known in the art (Methods of Enzymology, Vol. 153, (1987)).

According to a preferred embodiment of the present invention, the transformant may be a plant or a microorganism.

The IbENOD93 gene according to the present invention may be introduced into any plant in which the thickening growth of storage root is to be promoted.

According to a preferred embodiment of the present invention, the plant may be a herbaceous plant having storage root(s).

According to a preferred embodiment of the present invention, the herbaceous plant having storage root(s) may be selected from the group consisting of ginseng, *Codonopsis lanceolata, Ostericum koreanum* Kitagawa, *Platycodon grandiflorum, Pueraria thunbergiana, Aralia continentalis* Kitagawa, *Ledebouriella seseloides, Angelica gigas* Nakai, carrot, sweetpotato, dahlia, beet, maca, lily, tulip, and cassava.

According to the present invention, the IbENOD93 gene promotes the thickening growth of storage root of a plant, and thus the transgenic plant of the present invention has storage root(s) with enhanced thickening growth compared to wild-type plants.

One skilled in the art may culture or cultivate a transgenic plant cell or seed under appropriate conditions to allow it to grow to a plant.

As used herein, the term "plant" should be understood to encompass mature plants as well as plant cells, plant tissues, and plant seeds that can grow to mature plants.

According to a further aspect of the present invention, the present invention provides a composition for enhancing root thickening growth and promoting maturation in a herbaceous plant having storage root(s), the composition comprising at least one selected from the group consisting of a gene comprising the nucleotide sequence of SEQ ID NO.: 1, an ORF comprising the nucleotide sequence of SEQ ID NO.: 3, a vector comprising the gene or the ORF, and a protein comprising the amino acid sequence of SEQ ID NO.: 2.

With the administration of the composition to a plant and the transfection of the plant with the composition, it is possible to express the gene associated with root thickening growth or increase the expression, thereby increasing the thickening growth and maturation of the storage root.

According to a preferred embodiment of the present invention, the composition may further comprise auxin or jasmonic acid to induce the expression of the gene.

The expression of the IbENOD93 gene according to the present invention may be induced by exogenously applied auxin or jasmonic acid to promote the thickening growth of the storage root. It is preferred that the auxin or jasmonic acid is applied at a predetermined concentration for a predetermined period of time. For example, the concentration of the auxin or jasmonic acid may preferably be 500 and 100 μM, respectively. These hormones may preferably be applied for 3 hours at a proper concentration.

According to another further aspect of the present invention, the present invention provides a method for producing a transgenic plant having a storage root with enhanced thickening growth, the method comprising the steps of:

(a) inserting a gene comprising the nucleotide sequence of SEQ ID NO.: 1 or an ORF comprising the nucleotide sequence of SEQ ID NO.: 3 into a plant expression vector and then introducing the resulting vector into a plant; and (b) obtaining a transgenic plant having storage root(s) with enhanced thickening growth from the plant of the (a).

The transformation of a transgenic plant according to the present invention is determined by a method well known in the art. For example, when PCR is performed using DNA samples obtained from tissues of the transgenic plant, a foreign gene inserted into the genome of the transgenic plant can be identified. Alternatively, the transformation may be determined by either Northern or Southern blotting (Maniatis et al., Molecular Cloning, A Laboratory Manual, Cold Spring Harbor Laboratory, Cold Spring Harbor, N.Y. (1989)).

According to still another further aspect of the present invention, the present invention provides a method for regulating or enhancing root thickening growth and maturation in a plant having storage root(s), the method comprising the steps of:

(a) inserting a gene comprising the nucleotide sequence of SEQ ID NO.: 1 or an ORF comprising the nucleotide sequence of SEQ ID NO.: 3 into a plant expression vector and then introducing the resulting vector into a plant; and (b) obtaining a transgenic plant having storage root(s) with enhanced thickening growth from the plant of the (a).

Moreover, according to a preferred embodiment of the present invention, the method may further comprise, after step (b), the step of inducing the expression of the gene by treating the plant with auxin or jasmonic acid.

According to the present invention, the method is to promote the thickening growth of the storage root of the plant, comprising the step of inserting an IbENOD93 gene into a plant expression vector and then introducing the resulting vector into a plant, and when the thickening growth of the storage root is promoted as mentioned above, it is possible to shorten the cultivation period of high-value storage root crops such as ginseng and accordingly to reduce the damage due to root disease, thereby improving the productivity of root crops.

According to yet another further aspect of the present invention, the present invention provides a method for regulating the development of storage root of a plant, the method comprising the step of inducing the expression of an IbENOD93 gene comprising the nucleotide sequence of SEQ ID NO.: 1 by treating the plant with auxin or jasmonic acid.

The method can be applied to a transformant constructed to express the gene as well as a plant having storage roots with the gene such as sweet potato. That is, the method of the present invention is to regulate the development of the storage root of the plant by inducing the expression of the gene with the application of auxin or jasmonic acid.

The composition and method of the present invention use the above-described gene, vector, and transformant, and thus a repeated description will be omitted to avoid undue redundancy leading to the complexity of this specification.

BRIEF DESCRIPTION OF THE DRAWINGS

The above and other features and advantages of the present invention will become more apparent by describing in detail exemplary embodiments thereof with reference to the attached drawings in which:

FIG. 1A shows sweet potato tissues used to examine the expression pattern of a sweet potato IbENOD93 gene according to the present invention and FIG. 1B shows the expression pattern in a sweet potato plant.

FIG. 3 shows the expression pattern of the sweet potato IbENOD93 gene according to the present invention in a storage root, in which FIGS. 3A, 3B, and 3C show the cross-section of a young storage root of sweet potato, FIGS. 3D, 3E, and 3F show the cross-section of a young storage root of sweet potato hybridized with a sense riboprobe, and FIGS. 3G, 3H, and 3I show the cross-section of a young storage root of sweet potato hybridized with an anti-sense riboprobe; wherein PC stands for primary cambium; SC stands for secondary cambium; and PH stands for primary phloem.

DETAILED DESCRIPTION OF THE INVENTION

Figure 2A:
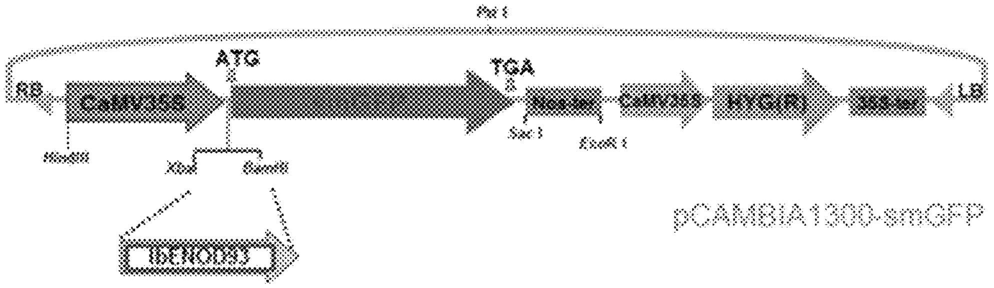
FIG. 2A shows the structure of a binary vector constructed to determine the cellular localization of an IbENOD93 protein produced by the sweet potato IbENOD93 gene according to the present invention and FIG. 2B shows the cellular localization.

Hereinafter, the present invention will be described in detail with reference to Examples. However, the following Examples are intended to illustrate the present invention, and the present invention is not limited by the following Examples.

Example 1: Analysis of Nucleotide Sequence of Sweet Potato IbENOD93 cDNA

RNA was isolated from young tuberous roots of sweet potato, an expressed sequence tag (EST) library was constructed with the isolated RNA, and then 2,859 ESTs were cloned and registered in the NCBI (NCBI accession numbers: BU690119-BU692977, You et al., 2003, FEBS Letters 536, 101-105). Among these ESTs, a cDNA with high homology to an ENOD93 protein was isolated, and it was found that the nucleotide sequence of the cDNA consists of 577 bp, including a 5'-untranslated region of 75 bp, an open reading frame (ORF) of 312 bp (103 amino acids), and a 3'-untranslated region of 190 bp. The ORF nucleotide sequence was registered as "cDNA sequence of IbENOD93 cloned from sweetpotato" in the NCBI (NCBI accession no. KC915011).

Example 2: Analysis of Expression Pattern of IbENOD93

(1) Northern Blotting Analysis

To determine the expression pattern of IbENOD93, total RNA was isolated from various tissues, including the fibrous root (FR, diameter <0.2 cm) before the development of storage root (FR stage), the young storage root (YSR, diameter 0.5~1.0 cm) in the early stage of the storage root development (YSR stage), and the fibrous root (FR-MSR) and mature storage root (diameter >5.0 cm) after the complete growth of storage roots (MSR stage) (see FIG. 1A). Total RNA extraction was performed using a 4.4 M guanidinium-SDS lysis buffer (Chirgwin et al., 1979) and 5.7 M CsCl gradient method (Glisin et al., 1974), and then about 25 μg of the extracted total RNA was electrophoresed on 1% agarose-formaldehyde gel and transferred onto a Tropilon-Plus™ nylon membrane (Tropix, USA).

A probes was prepared by amplification of a plasmid (2.5 ng) containing a 577-bp IbENOD93 cDNA, through PCR, which was performed in a PCR mixture containing 100 μM of dNTP mix exclusive of dCTP, 100 μM of dCTP-biotin, 10 μM of vector (pBluescript II) primers T3 (5'-AATTAACCCTCACTAAAGGG-3', SEQ ID NO.: 5) and T7 (3'-CGGGATATCACTCAGCATAATG-5', SEQ ID NO.: 6) each, 1×PCR buffer and 1 unit of Taq polymerase to a final volume of 10 μl, starting with pre-denaturation at 95° C. for 5 minutes, with 30 cycles of denaturation at 95° C. for 30 seconds, annealing at 58° C. for 20 seconds, and extension at 72° C. for 30 seconds.

The PCR-amplified biotinylated probe was purified using a QIAquick™ PCR purification kit (QIAGEN, Germany) and was added in an amount of about 100 ng onto the membrane, followed by hybridization at 65° C. or 68° C. for 18 hours. The membrane was washed twice with 2×SSC/1% SDS at room temperature for 5 minutes, then twice with 0.1×SSC/1% SDS at room temperature for 15 minutes, and finally twice with 1×SSC at room temperature for 5 minutes. Probe detection was performed using a Southern-Star™ kit (Tropix, USA). The blots were treated with a blocking buffer (1×PBS, 0.2% I-Block™ Reagent and 0.5% SDS) and labeled with alkaline phosphatase-conjugated streptavidin, followed by treatment with CDP-Star™ (Ready-to-Use). The membrane was exposed to an X-ray film (Fujifilm, Japan) for a period ranging from 10 minutes to 1.5 hours.

(2) Determination of Expression Pattern of IbENOD93

The expression of IbENOD93 was detected in the fibrous root tissue before the development of storage root, and the expression level was increased in the young storage root in the early stage of the development of storage root. However, no expression was detected in the fibrous root tissue after the complete growth of storage root. Low expression was detected in leaf tissues before the development of storage root and in stem tissues in an early storage root stage (See FIG. 1B). That is, these expression patterns suggest that IbENOD93 is mainly expressed in the root and the expression level further increases in the early stage of the development of storage root.

Example 3: Analysis of Cellular Localization of IbENOD93 Gene

To determine the cellular expression localization of IbENOD93, agroinfiltration of tobacco leaves was performed. The IbENOD93 cDNA was inserted between restriction enzymes XbaI and BamHI in the multicloning site of pCAMBIA1300 vector (pCMABIA1300-smGFP) modified by insertion of a CaMV 35S promoter and GFP.

To amplify the coding sequence of IbENOD93 (309 bp) using PCR, an XbaI restriction enzyme recognition site was added to the 5'-primer (ENOD(1)F-XbaI 5'-GTCTCTAGAATTGAACAAAACATAGCTTTTTCTTGAATTT-3', SEQ ID NO.: 7) and a BamHI restriction enzyme recognition site was added to the 3'-primer (ENOD(373)R-BamHI 5'-GTAGGATCCCATCAATGTTGGCGGAG-3', SEQ ID NO.: 8), followed by PCR amplification.

The resulting PCR product was fused in-frame to smGFP and introduced into pCMABIA1300-smGFP vector (FIG. 2A), and then transformed into *agrobacterium* GV3101 for agroinfiltration. Tobacco leaves grown in the greenhouse for one month were used for agroinfiltration analysis. The *agrobacterium* containing the targeting vector was cultured in 2 mL YEP liquid medium at 28° C. overnight. 500 μl of culture medium was cultured in 50 mL YEP liquid medium to $OD_{600}$ of 1.0 and then centrifuged at 5000 g for 5 minutes at room temperature, and the supernatant was removed.

The precipitate was suspended by adding 50 mL infiltration buffer [10 mM $MgCl_2$, 10 mM MES-KOH (pH 5.7), 200 μM Acetosyringone] and centrifuged again under the same conditions, the supernatant was removed, and the infiltration buffer was added again at $OD_{600}$ of 1.0. The culture medium at $OD_{600}$ of 1.0 was left at room temperature for 2 to 4 hours and then infiltrated into tobacco leaves using a syringe. The leaves were collected 2 to 3 days after agroinfiltration, and then the position of GFP was determined using a confocal microscope (LSM 700; Carl Zeiss).

Figure 2B:
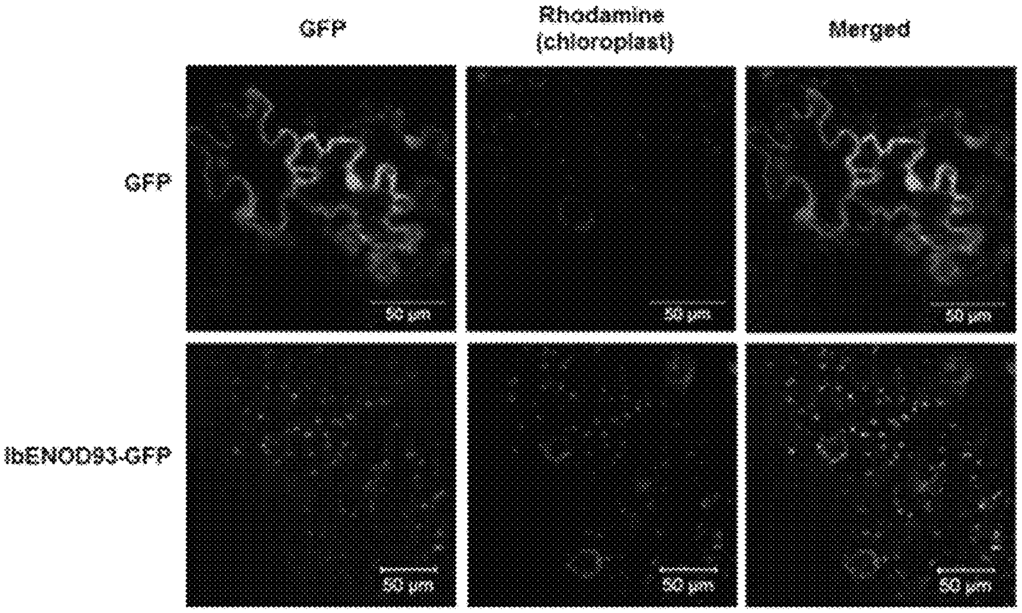

Fluorescence of GFP was observed in the cytoplasm and nucleus in the control (GFP), but the IbENOD93 showed a pattern different from the control, and rhodamine staining results showed that the position of the chloroplast coincided with the cellular localization of IbENOD93 protein (FIG. 2B). These results suggest that the IbENOD93 protein is located on the plasmid of the plant.

Example 4: Analysis of Localization of IbENOD93 Gene in Storage Root

In situ hybridization was performed to determine the localization of IbENOD93 in storage roots. To this end, storage roots (0.5 cm in diameter) were cut transversely and fixed in FAA solution (containing 50% ethanol, 5% acetic acid, and 3.7% formaldehyde) at 4° C. for 10 days. Then, the samples were dehydrated stepwise for 30 minutes in increasing concentrations of ethanol (50, 60, 70, 80, 90, 95, and 100%), embedded in paraffin for 5 days, and sectioned into 10 μm thick slices. The sections were treated with xylene followed by a series of treatments (hydration, proteinase K treatment, acetylation, and dehydration). For the in situ hybridization, the full-length sequence of IbENOD93 was used to synthesize sense and antisense IbENOD93 probes labeled with digoxigenin-UTP using a DIG RNA labeling kit (Roche, Germany).

For this purpose, the sense probe was prepared from pBluescript II SK vector which was inserted IbENOD93 cDNA with BamHI, and the antisense probe was prepared from pBluescript II SK vector which was inserted IbENOD93 cDNA with KpnI. Then, T3 and T7 polymerases were used to synthesize RNA for 2 hours, respectively. The resultant was shear with $Na_2CO_3$ and $NaHCO_3$ at 60° C. for 40 minutes to obtain the desired-size probes.

Prehybridization was performed in a humid chamber at 42° C. for 2 hours, and then hybridization was performed in a humid chamber with hybridization buffer containing sense and antisense probes of IbENOD93 at 42° C. for 16 hours. Immunological detection was performed using an alkaline phosphatase-coupled anti-DIG antibody (Roche, Germany). Violet slices were photographed with a fluorescence microscope (OLYMPUS BX51, Japan).

Figure 3:
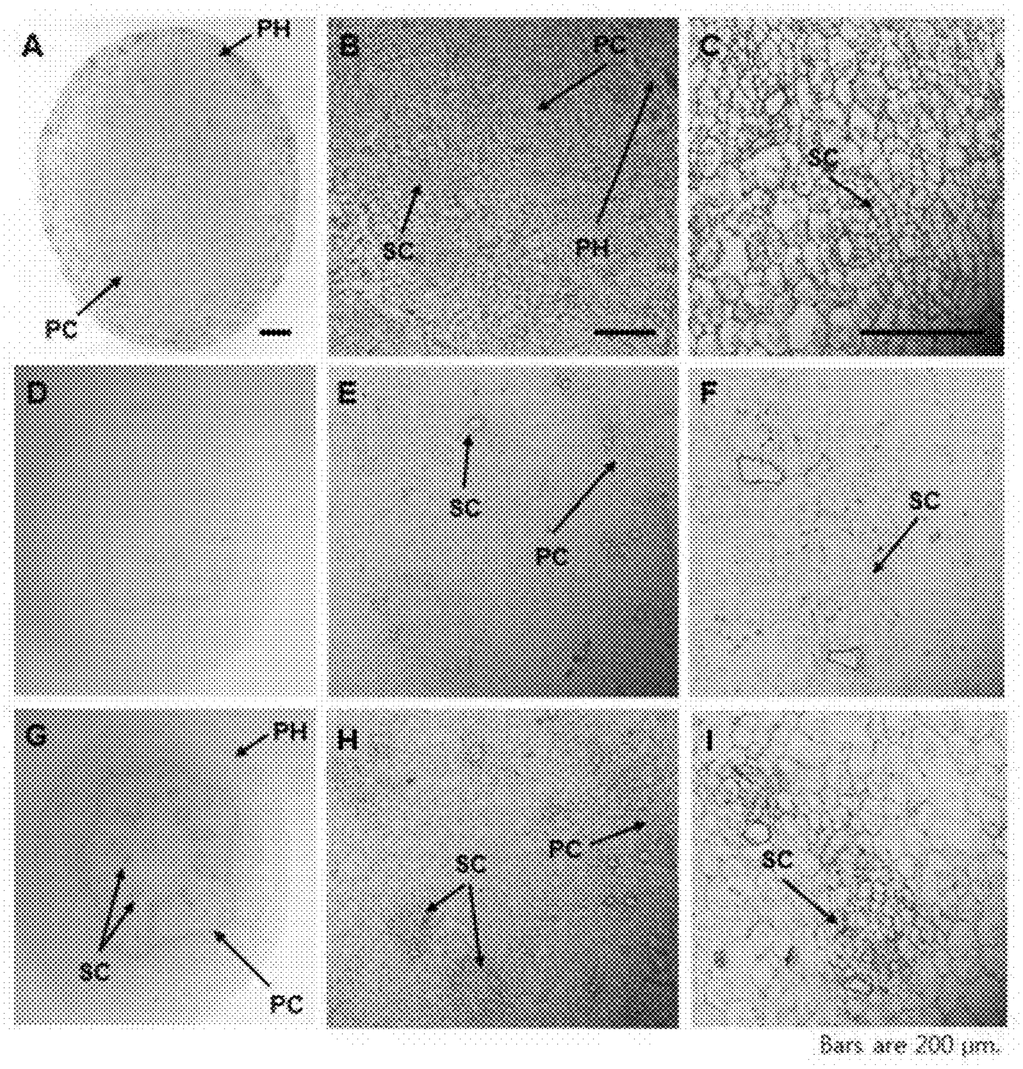

The mRNA of IbENOD93 was mainly distributed in the cambium of storage root, and among others, it was strongly expressed in the primary cambium (PC) and secondary cambium (SC) (FIG. 3). Given that the cell division occurs most actively in the primary cambium and secondary cambiums in the initial thickening growth of storage roots of sweet potato, these expression patterns suggest that the function of IbENOD93 is involved in the initial thickening growth of storage roots of sweet potato.

Example 5: Analysis of Regulation of IbENOD93 Expression by Treatment with Plant Hormone To determine the transcriptional regulation of IbENOD93 gene by treatment with auxin (Indole-3-acetic acid; IAA), jasmonic acid (JA), and cytosine (6-benzylaminopurine; BA), real-time PCR (RT-PCR) was performed using IbENOD93-specific primers (IbENOD93(360)F 5'-CATCATACTCATTACTCATACATCCAAACA-3' (SEQ ID. NO.: 9) and IbENOD93(512)R 5'-CAGTCTCCGCCAACATTGATG-3' (SEQ ID. NO.: 10)).

The roots of sweet potato were treated with hormones according to the following method. Sweet potato plantlets bearing a single leaf and petiole were collected from sweet potato plants and incubated in flasks filled with water for 3 weeks. After fibrous roots had developed from the distal end of the petiole, the single-leaf plantlets were incubated in various concentrations of IAA, JA, and BA solutions (0, 50, 100, 200, 500, 1000 μM) at 25° C. in the dark for 3 hours. After the hormone treatment, total RNA was extracted from the fibrous roots using the RNeasy Plant Mini Kit™ (Qiagen) and used for RT-PCR.

Total RNA (5 μg) was used for first-strand cDNA synthesis using the SuperScript III first-strand cDNA synthesis kit (Invitrogen). The resulting cDNA solution was then diluted with 30 μl of TE and used for PCR. Among a total of 20 μl, 1 μl of the synthesized cDNA was used for the RT-PCR, and KAPA SYBR FAST Master mix (KAPABIOSYSTEMS) was used for a final reaction volume of 16 μl. Real-time PCR analysis was performed using the LightCycler 480 quantification system (Roche Diagnostics) according to the manufacturer's instructions. Expression levels were normalized with β-tubulin expression amplified with 5'-CAACTACCAGCCACCAACTGT-3' (SEQ ID. NO.: 11) and 5'-CAGATCCTCACGAGCTTCAC-3' (SEQ ID. NO.: 12) primers. Real-time PCR was performed starting with pre-denaturation at 95° C. for 10 minutes, followed by 45 cycles of denaturation at 95° C. for 10 seconds, annealing at 58° C. for 10 seconds, and extension at 72° C. for 20 seconds. Following the amplification phase, a melting curve analysis was conducted from 65° C. to 97° C. The second derivative maximum method in the LightCycler 480 quantification software (Roche Diagnostics) was used to evaluate the data.

Figure 4:
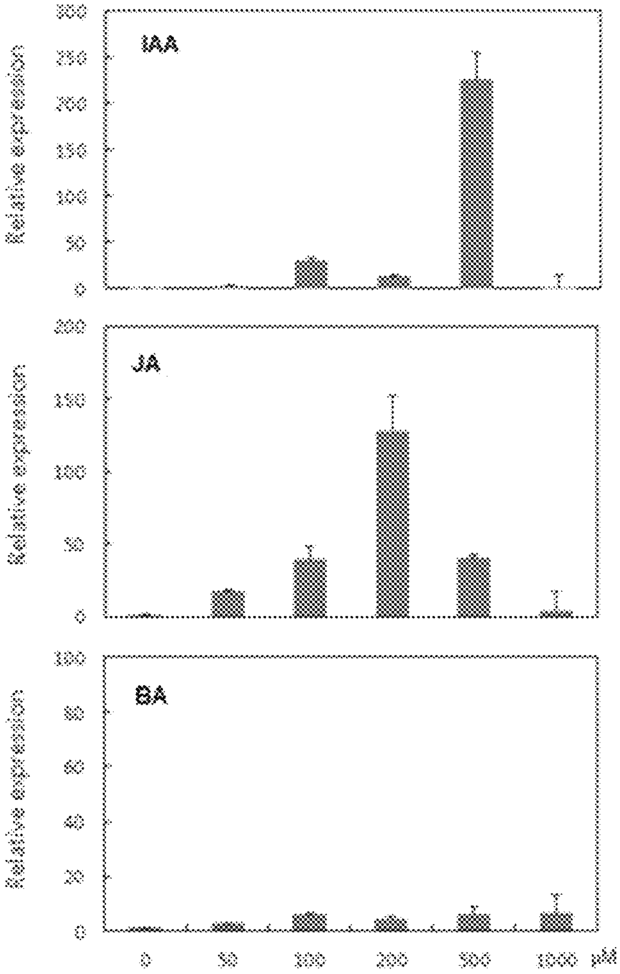
FIG. 4 shows that the expression of the sweet potato IbENOD93 gene according to the present invention is regulated by exogenously applied IAA, JA, and BA.
Figure 5:
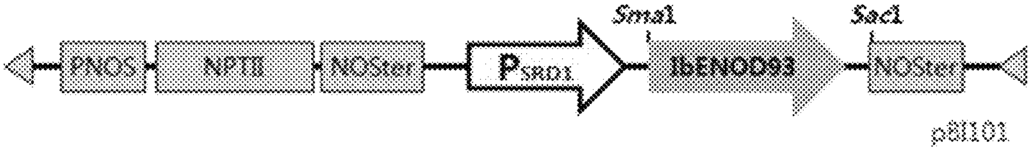
FIG. 5 shows the structure of a binary vector constructed to overexpress the sweet potato IbENOD93 gene according to the present invention in carrot.

Upon treatment with various concentrations of IAA, JA, BA (0, 50, 100, 200, 500, 1000 μM) for 3 hours, the IbENOD93 mRNA levels were regulated (FIG. 4), and the transcript level of IbENOD93 increased sharply at 500 μM IAA and 200 μM JA. On the contrary, in the BA treatment, the transcript level of IbENOD93 increased slightly at 100 μM or higher. Meanwhile, it was reported that upon IAA or JA treatment of MADS-box genes (SRD1, IbMADS1)

which were found to promote the initial thickening growth of storage roots of sweet potato, the transcript level increased sharply (Noh et al., 2010, Journal of Experimental Botany 61, 1337-1349; Ku et al., 2008, Annals of Botany 102, 57-67). Based on these results, the sharp increase in the transcript level of IbENOD93 by the IAA and JA treatment suggests that the IbENOD93 gene can promote the thickening growth of storage roots of sweet potato.

Example 6: Production of Binary Vector and Transformation of Carrot

To analyze the functions of the IbENOD93 gene involved in the development of storage root in carrot, a binary vector for overexpression was prepared. A transformation binary vector was prepared by operatively linking IbENOD93 to an SRD1 promoter (Noh et al., 2012, Transgenic Research 21, 265-278; Korean Patent No.: 10-0604186; U.S. Pat. No. 7,273,967; Japanese Patent No.: 4233569; Chinese Patent No.: ZL200480024420.8; Canadian Patent No.: 2,544,798), which is a root-specific expression promoter that has been developed by the present inventors to induce the expression of IbENOD93 in a storage root-specific manner, followed by insertion into pBI101. For this purpose, the GUS gene was deleted from the pBI101 vector into which the pre-prepared 3.0 kb SRD1 promoter was inserted, and the IbENOD93 gene of sweet potato was inserted into the site. A SmaI restriction enzyme recognition site was added to the 5'-primer of the IbENOD93 gene (5'-CATCCCGGGATTGAACAAAACATAGCT-3', SEQ ID NO.: 13) and a SacI restriction enzyme recognition site was added to the 3'-primer (5'-CATGAGCTCCATTGTTGGTCATACAACA-3', SEQ ID NO.: 14), followed by PCR amplification.

The thus prepared vector, $P_{SRD1}$-IbENOD93, was transformed into *agrobacterium* LBA4404, which was then cultured in M9 medium for 2 days and used as co-culture for transformation. Carrot seeds (Hapa-Ochon, Syngenta Seeds) were germinated on MS medium, and when the hypocotyl grew to 0.5 to 1.0 cm in size, the hypocotyl was cut and incubated on MS liquid medium at 25° C. in the dark for 2 days. The *agrobacterium* LBA4404 cultured in M9 medium was harvested by centrifugation and co-cultured in MS liquid medium together with the cultured hypocotyl for 5 to 10 minutes, washed with fresh MS liquid medium, and transferred to MS medium supplemented with 2,4-D to induce embryogenic calli. The induced embryogenic calli were transferred to medium supplemented with kanamycin and 2,4-D and passaged every 3 to 4 weeks, and transformed calli were selected. Embryogenic calli were induced from the transformed calli, and then the carrot plants were regenerated on MS medium without 2,4-D. Then, when the aerial parts grew to 5 to 10 cm, the plants were transferred to soil and grown in a growth chamber at 25° C. and under 16/8 h (light/dark) conditions after domestication.

Figure 6:
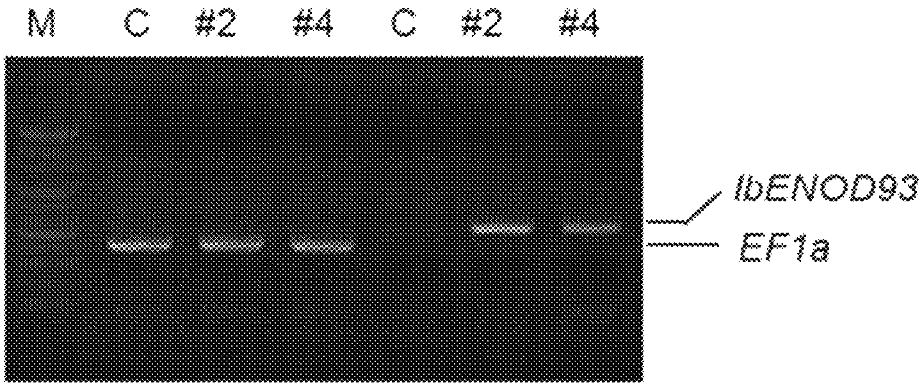
FIG. 6 shows the gene insertion in transgenic carrot plants into which the sweet potato IbENOD93 cDNA according to the present invention is inserted, wherein M represents the size marker; C represents the control (a plant transformed only with a pBI101 vector); #2 represents IbENOD93 transformant line #2; and #4 represents IbENOD93 transformant line #4.

Example 7: Identification and Expression Analysis of Transgenic Carrot Plants Genomic DNA was extracted to identify the insertion of the IbENOD93 gene in transgenic carrot. When transgenic carrot plants grown in vitro produced 3-4 leaves, the leaves were extracted with 600 μl of extraction buffer (200 mM Tris-pH 7.5, 250 mM NaCl, 25 mM EDTA, 0.5% SDS), frozen in LN2, and homogenized. After centrifugation, 500 μl of supernatant and 500 μl of isopropanol were added and precipitated. Pellets obtained by centrifugation were washed and dissolved in 30 μl of TE buffer. Primers were prepared to perform genomic PCR to identify transformants, followed by in vitro growth. PCR analysis to identify transformants was performed by the following method. 3 μl of genomic DNA was used as template DNA, and 2 units of iTaq polymerase (Intron) were used in a 20 μl reaction volume. Carrot elongation factor 1-alpha (EF1a) primers (5'-GGAACCTCTCAGGCTGATTGTG-3' (SEQ ID. NO.: 15) and 5'-ACAATTTCCTCAAATCTAGACTTGGAA-3' (SEQ ID. NO.: 16)) and inserted IbENOD93 gene-specific primers (5'-CATCCCGGGATTGAACAAAACATAGCT-3' (SEQ ID. NO.: 13) and 5'-CATGAGCTCCATTGTTGGTCATACAACA-3' (SEQ ID. NO.: 14)) were used to identify transformants. PCR amplification was performed by completely denaturing the genomic DNA for 3 minutes, followed by 35 cycles of denaturation at 95° C. for 30 seconds, annealing at 55° C. for 30 seconds, and extension at 72° C. for 30 seconds, with a final extension at 72° C. for 10 minutes. The PCR products were electrophoresed on 1.3% agarose gel, and the PCR products corresponding to the EF1a gene (400 bp) and the IbENOD93 gene (530 bp) were detected. The carrot EF1a gene was observed both in the control (C: carrot transformed only with a pBI101 vector) and in transgenic plants #2 and #4 into which IbENOD93 was inserted. However, the IbENOD93 gene was not detected in the control, but was detected in IbENOD93 transgenic carrot plants #2 and #4 (FIG. 6). These results suggest that the IbENOD93 gene is inserted into the genomes of transgenic carrot plants #2 and #4.

Figure 7:
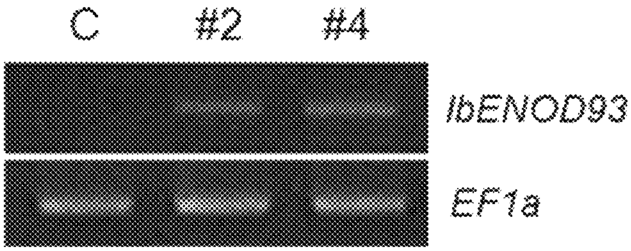
FIG. 7 shows the expression of an IbENOD93 gene in transgenic carrot plants into which the sweet potato IbENOD93 cDNA according to the present invention is inserted, wherein C represents the control (a plant transformed only with a pBI101 vector); #2 represents IbENOD93 transformant line #2; and #4 represents IbENOD93 transformant line #4.

To identify the expression of the IbENOD93 gene inserted into the transgenic carrot plants, total RNA was extracted from the transgenic plants grown in vitro for 3 months. About 100 mg of root tissue was mixed with 500 μl of Trizol, and frozen in LN2, and the frozen tissue homogenized. 250 μl of Chloroform was added and centrifuged and 500 μl of supernatant and 500 μl of isopropanol were added and precipitated. Pellets obtained by centrifugation were washed and dissolved in 30 μl of RNase-free water. cDNA was synthesized from 5 μg of total RNA per sample using RevertAid Reverse Transcriptase (MBI Fermentas, # EP0441). After the synthesis, a ⅕ dilution of the cDNA was used for PCR. PCR analysis was performed using the EF1a primers and the inserted IbENOD93 gene-specific primers, starting with pre-denaturation at 95° C. for 3 minutes, with 35 cycles of denaturation at 95° C. for 30 seconds, annealing at 55° C. for 30 seconds, and extension at 72° C. for 30 seconds, with a final extension at 72° C. for 10 minutes. The PCR products were electrophoresed on 1.3% agarose gel, and the PCR products corresponding to the EF1a gene (400 bp) and the IbENOD93 gene (530 bp) were detected. The mRNA of the IbENOD93 gene was not observed in the control (C: carrot transformed only with a pBI101 vector), but was detected in transgenic carrot plants #2 and #4 (FIG. 7). These results suggest that the inserted IbENOD93 sweet potato gene is expressed in carrot root tissues.

Example 8: Growth Analysis of Transgenic Carrot Roots

Figure 8A:
FIGS. 8A and 8B show the comparison of the root growth of transgenic carrot plants grown in vitro, into which the sweet potato IbENOD93 (cDNA) according to the present invention is inserted, with the control, wherein C represents the control (a plant transformed only with a pBI101 vector); #2 represents IbENOD93 transformant line #2; and #4 represents IbENOD93 transformant line #4.
Figure 8B:
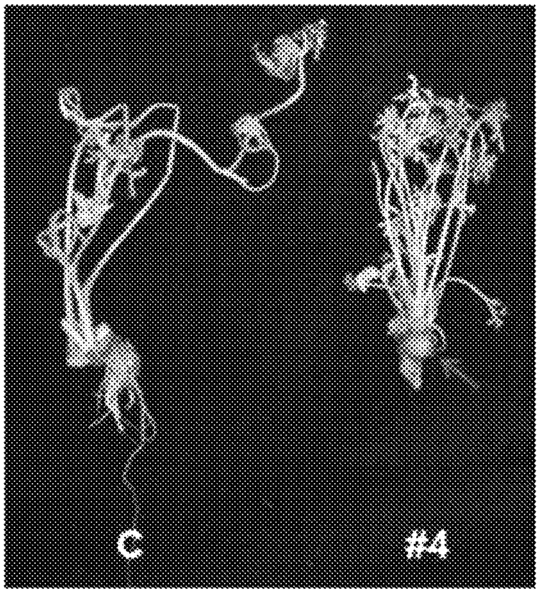

Hypocotyl of carrot transformed with the $P_{SRD1}$-IbENOD93 vector was cultured in selective medium supplemented with kanamycin and 2,4-D to induce embryogenic calli, and the selected embryogenic calli were regenerated in MS medium without 2,4-D into carrot plants. When the aerial parts of plantlets were regenerated from the calli, each plant was transferred to magenta box containing about 200 ml of MS medium and continuously grown to induce the growth of taproot. After in vitro growth for 3 months, the media was removed, and the difference in development of taproots between the transgenic plants and the control was observed. At this time, the carrot plant transformed with the pBI101 vector used for the production of the $P_{SRD1}$-IbENOD93 vector was used for the control (C). Growth patterns of the taproots were compared between the control and the IbENOD93-transgenic plants, and it was found that the diameter of the taproot of the IbENOD93-transgenic carrot plant was significantly increased compared to the diameter of the root of the control (FIGS. 8A-8B). The diameter of the taproot of the IbENOD93-transgenic plant was 11.0±2.0 mm, while the diameter of the control was 2.7±0.7 mm (Table I). These results suggest that the thickening growth of the taproot of the IbENOD93-transgenic plant is significantly faster than the thickening growth of the taproot of the control, and the taproot thickening growth pattern is a common phenotype that occurs in two lines (#2 and #4) of the IbENOD93 transgenic plants.

TABLE I

| | Control | IbENOD93 |
|---|---|---|
| Root diameter (mm)[a] | 2.7 ± 0.7 | 11.0 ± 2.0 |

[a]Determined by measuring the largest diameter

Example 9: Analysis of Storage Root Production in Transgenic Carrot

Figure 9A:
FIGS. 9A to 9C show the comparison of the root growth of transgenic carrot plants grown in soil, into which the sweet potato IbENOD93 (cDNA) according to the present invention is inserted, with the control.
Figure 9B:
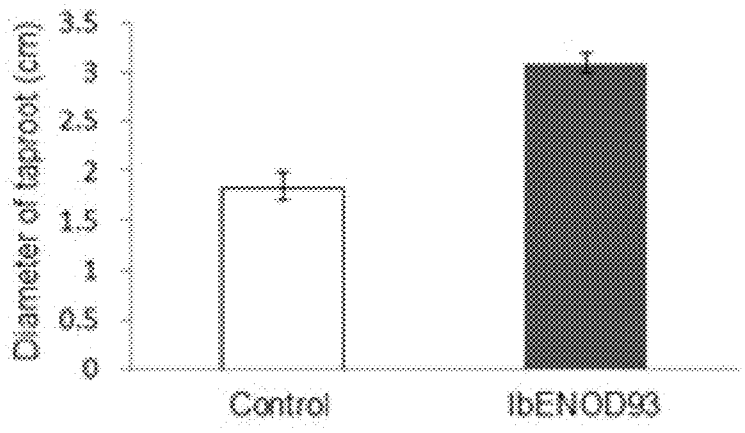
Figure 9C:
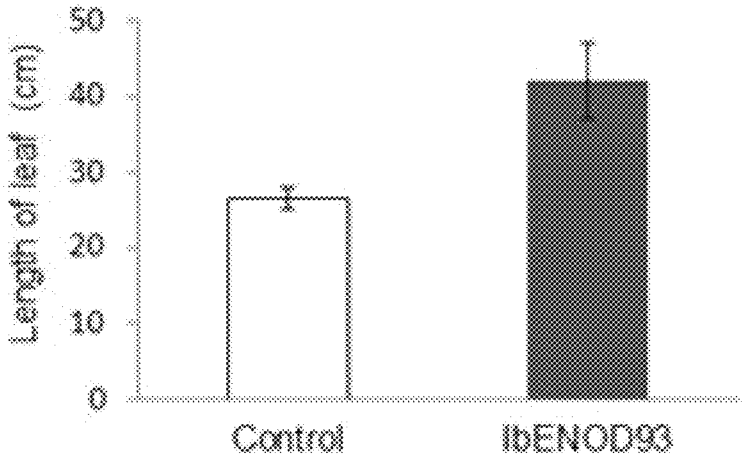

To examine the storage root production in transgenic carrot plants, the regenerated transgenic plantlets were transferred to soil and grown in a growth chamber for 3 months after domestication. It was found that the thickening growth of storage root was promoted in the IbENOD93 transgenic plant, compared to the control (transgenic plant with the pBI101 vector) (FIG. 9A). Consequently, the diameter of the storage root of the IbENOD93 transgenic plant (3.1±0.1 cm) was increased about 1.7 times compared to the diameter of the storage root of the control (1.83±0.13 cm) (FIG. 9B). Moreover, the growth of aerial part was also promoted in the IbENOD93-transgenic plant comparing to that in the control. Leaf length was 42.0±5 cm in IbENOD93 transgenic plant but 26.5±1.5 cm in the control, resulting in 1.6 times increase in leaf length in IbENOD93 transgenic plant (FIG. 9C). Based on the fact that the IbENOD93 gene in the IbENOD93 transgenic plants is under the control of the SRD1 promoter that induces storage root-specific expression of carrot, these results suggest that the expression of the IbENOD93 gene in storage root tissues promotes the thickening growth of storage roots, which in turn promotes the growth of aerial parts. Consequently, early-maturing transgenic carrot plants were produced by expressing the IbENOD93 gene involved in the thickening growth of storage roots.

Therefore, the IbENOD93 cDNA according to the present invention can be effectively used for the production of transgenic plants in which the development of storage roots and aerial parts is promoted.

As described above, the present invention provides the sweet potato (*Ipomoea batatas*)-derived IbENOD93 gene, which promotes the thickening growth of storage roots as well as the growth in aerial part. Therefore, the present invention can be effectively used for the development of high-value early-maturing transgenic root crops such as ginseng, sweet potato, etc.

While the invention has been shown and described with reference to certain preferred embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims and their equivalents.

What is claimed is:

1. A method for producing a transgenic plant having storage root(s) with enhanced thickening root growth, the method comprising the steps of:

(a) inserting a promoter comprising the nucleotide sequence of SEQ ID NO.: 4; and a gene comprising: the nucleotide sequence of SEQ ID NO.: 1 or an ORF comprising the nucleotide sequence of SEQ ID NO.: 3 into a plant expression recombinant vector, wherein the promoter is operably linked to the gene;

(b) introducing the plant expression recombinant vector of step (a) into a plant;

(c) selecting the plant of step (b) if the plant has storage root(s) with enhanced thickening growth; and (d) obtaining a transgenic plant having storage root(s) with enhanced thickening growth from the selected plant of step (c).

2. The method of claim 1, further comprising, after step (d), a step of increasing the expression of the gene operably linked to the promoter comprising the nucleotide sequence of SEQ ID NO.: 4 by treating the plant with auxin or jasmonic acid.

* * * * *